United States Patent [19]

Cuca

[11] Patent Number: 5,002,777

[45] Date of Patent: Mar. 26, 1991

[54] ENCAPSULATED ANTACID

[75] Inventor: Robert C. Cuca, Edwardsville, Ill.

[73] Assignee: Norcliff Thayer Inc., St. Louis, Mo.

[21] Appl. No.: 928,104

[22] Filed: Nov. 9, 1986

Related U.S. Application Data

[62] Division of Ser. No. 877,793, Jun. 24, 1986, Pat. No. 4,656,028.

[51] Int. Cl.$^5$ .............................................. A61K 33/10
[52] U.S. Cl. ................................................... 424/687
[58] Field of Search ................. 427/154, 156; 424/687

[56] References Cited

U.S. PATENT DOCUMENTS

| 3,253,988 | 5/1966 | Scott | 424/156 |
| 3,843,778 | 10/1974 | Diamond et al. | 424/156 |
| 4,140,760 | 2/1979 | Withington | 424/156 |
| 4,255,413 | 3/1981 | Rattie et al. | 424/452 |
| 4,271,142 | 6/1981 | Puglia et al. | 424/156 |
| 4,486,412 | 12/1984 | Shah et al. | 424/154 |
| 4,542,019 | 9/1985 | Lezdey | 424/156 |
| 4,656,028 | 4/1987 | Cuca | 424/37 |

*Primary Examiner*—Shep K. Rose
*Attorney, Agent, or Firm*—Jacobs & Jacobs, Inc.

[57] ABSTRACT

A concentrated suspension of calcium carbonate particles in a liquid carrier that is compatible with a capsule shell material. The suspension is pourable and pumpable and may be used to provide antacid capsules.

9 Claims, 1 Drawing Sheet

ENCAPSULATED ANTACID

This is a division of our copending application Ser. No. 877,793, filed June 24, 1986, now U.S. Pat. No. 4,656,028, issued Apr. 7, 1987.

The present invention relates to antacid capsules, and more particularly to capsules containing a concentrated liquid suspension of calcium carbonate.

Aqueous antacid suspensions are widely distributed as over the counter products for neutralizing excess stomach acid. However, some users develop a dislike to the taste, grittiness and chalky "mouthfeel" of these liquid suspensions. While gelatin capsules are often used for the oral administration of unpleasant tasting medicaments, aqueous liquid suspensions cannot be capsulated within a gelatin capsule because they would deform or even rupture the gelatin.

Lachman et al, "*The Theory and Practice of Industrial Pharmacy*", Second Edition, 1976, published by Lea & Febiger, Philadelphia, describe in pages 404–420 the manufacture and use of one-piece soft gelatin capsules as oral dosage forms of a wide variety of liquids and solids. Aqueous antacid suspensions cannot be capsulated in gelatin capsules, because liquids containing even as little as 5% water migrate through the gelatin shell causing deformation or rupture thereof. However, non-aqueous antacid suspensions can be capsulated, and Lachman et al disclose, in page 412, antacid suspensions suitable for capsulation in soft gelatin capsules, namely suspensions of aluminum hydroxide and magnesium carbonate in a pharmaceutically acceptable liquid carrier compatible with gelatin. In particular, Lachman et al describe the use of vegetable oil or PEG 400 as typical pharmaceutically acceptable carriers for antacid suspensions suitable for capsulation in soft gelatin capsules. Shah et al U.S. Pat. No. 4,486,412, filed March 15, 1983, also disclose soft gelatin capsules containing antacid suspensions in polyethylene glycols, such as PEG 400.

However, the antacid suspensions proposed by Lachman et al and Shah et al for capsulation are not sufficiently concentrated to provide a capsule that is both of reasonable size and capable of neutralizing 15 mEq. of hydrochloric acid. Thus, the antacid suspensions proposed by Lachman et al contain at most 35% antacid, but a 35% calcium carbonate suspension would require the use of more than about 2100 mg of suspension to neutralize 15 mEq. of hydrochloric acid per capsule. Similarly, Shah et al disclose a calcium carbonate suspension containing only 51% calcium carbonate. To neutralize 15 mEq. of hydrochloric acid, the Shah et al capsules would have to contain about 1500 mg of the calcium carbonate suspension. Capsules that contain about 1500 to 2100 mg. of antacid suspension are so large as to be difficult to swallow.

Efforts to provide more concentrated suspensions of calcium carbonate provide to be unsuccessful, because the resulting suspensions could not be pumped. Surprisingly, it has now been found that the use of particles of calcium carbonate of specified size and shape provides pourable antacid suspensions that can be pumped with a standard positive displacement pump conventionally used for filling soft gelatin capsules. Hence, antacid capsules can now be manufactured commercially at a concentration of antacid not heretofore possible. For example, the present invention is able to provide liquid antacid capsules with at least 15 mEq. acid neutralizing capacity per capsule in a volume of only 0.6 ml, which is almost six times the neutralization capacity of common aqueous liquid antacid suspensions. In addition, the liquid antacid capsules of the invention are greatly reduced in size for a given acid neutralizing capacity as compared to the antacid capsules of Lachman et al. and Shah et al.

In particular, the present invention provides a pumpable slurry, which comprises from about 60 to about 70%, preferably from about 65 to about 70%, by weight, based on the weight of the slurry, of calcium carbonate particles suspended in a pharmaceutically acceptable liquid carrier that is compatible with an acid-or water-soluble capsule shell material and containing less than about 5% by weight of water, based on the weight of the liquid carrier, said calcium carbonate particles comprising more than about 50%, by weight, of particles in the range of from about 1 to about 10 microns, based on the weight of said particles, said calcium carbonate particles being irregularly shaped and having a plurality of edges formed by the intersection of substantially planar surfaces.

The present invention also provides capsules, preferably one-piece soft gelatin capsules, containing the antacid suspension defined above.

Control of the weight of particles within the range of from about 1 to about 10 microns provides the calcium carbonate slurry with the required rheology to be pumpable. As used herein, "pumpable" means a slurry that is pumpable by a positive displacement pump. If the amount of particles within the range of from about 1 to about 10 microns is about 50% by weight or less, the slurry is too viscous to pump and/or is too dilatant. As long as more than about 50% of the particles are within the range of from about 1 to about 10 microns, the remainder may be less than about 1 micron and/or more than about 10 microns. Preferably, no more than about 30% of the particles will be below about 1 micron or above about 10 microns, although it is preferred that the amount of particles above about 10 microns is minimized, such as from about 0 to about 10%. Preferably, at least about 65% of the particles will be in the range of from about 1 to about 10 microns, such as from about 70 to about 90% or more. In particular, it is preferred that the particle size distribution of the calcium carbonate particles comprise from about 75% to about 100% of particles in the range of from about 1 to about 10 microns, from 0% to about 15% of particles below 1 micron and from 0% to about 10% of particles above about 10 microns, all by weight based on the total weight of the particles.

The calcium carbonate particles used in the present invention must not only have the particle size distribution discussed above, they must also be irregularly shaped and have a plurality of edges formed by the intersection of substantially planar surfaces. The accompanying FIGURE is a photomicrograph at 5000X magnification of calcium carbonate particles that are useful in the present invention, and the distinctive shape of these particles is apparent. Calcium carbonate particles of suitable shape may be obtained by grinding limestone to the desired particle size. In contrast, precipitated calcium carbonate particles do not have a sharp-edged, irregular shape, but rather are generally spherical or ovoid. Calcium carbonate suspensions made with spherical or ovoid particles are too dilatant to be pumpable and hence do not give rise to the pourable and pumpable suspension of the present invention.

The antacid particles may be suspended in any pharmaceutically acceptable liquid carrier that is compatible with the water-and acid-soluble capsule shell, such as those disclosed by Lachman et al, supra, and other prior art, namely:

1. Water immiscible, volatile and non-volatile liquids, such as mineral, vegetable and aromatic oils, aromatic and aliphatic hydrocarbons, chlorinated hydrocarbons, ethers, esters, alcohols and organic acids.

2. Water miscible, non-volatile liquids, such as the polyethylene glycols, and non-ionic surface active agents, such as polysorbate 80.

3. Water miscible and relatively non-volatile liquids, such as glycerin, propylene glycol and isopropyl alcohol.

In general, the liquid carrier may contain up to 5% water, based on the total liquid. Pharmaceutically acceptable liquid carriers include vegetable oils with or without a surfactant, non-ionic surface active agents, mineral oils, medium chain triglycerides, acetylated glycerides and a polyethylene glycol or mixture of polyethylene glycols having an average molecular weight of from about 200 to about 1000, preferably from about 200 to about 600, such as PEG-400 and PEG-600. These liquids are useful in the present invention. Presently preferred capsule-compatible pharmaceutically acceptable liquid carriers are the polyethylene glycols defined above, as recommended by Lachman et al. for use with antacids.

The capsules containing the antacid suspension may be conventional one-piece or two-piece capsules, but the one-piece soft gelatin capsules are preferred. Lachman et al at pages 404–420 and Shah et al describe conventional procedures for preparing and filling soft gelatin capsules. The manufacture and filling of two-piece gelatin capsules is also well known.

If desired, the antacid suspension of the invention may include flavoring agents, such as an essential oil, and sweetening agents, such as sodium saccharin and the like. Preferably, the antacid may include a suspending agent, such as cross-linked carboxymethylcellulose sodium.

While it is preferred to use a gelatin capsule to capsulate the antacid suspension, other water and acid-soluble pharmaceutically acceptable capsules may be used, such as cellulose-derived polymeric capsules. The usual adjuvants, such as plasticizers, humectants, flavorants, colorants, opacifying agents, disintegrating agents and the like may be included, as desired, in the capsule shell.

The capsules may be filled with the antacid suspension using conventional encapsulation equipment. In the case of one-piece soft gelatin capsules, the capsules are filled with the antacid suspension using a rotary die encapsulation machine or other suitable machine, such as discussed in Lachman et al.

The antacid suspension may be prepared using conventional mixing equipment, such as a Cowles dissolver or preferably a high speed propeller mixer. After charging the mixer with the liquid carrier, any adjuvants are added, such as the suspending agent, flavorants and the like, while stirring, after which the calcium carbonate is added. Mixing is continued, preferably with scraping of the sides and bottom of the vessel, until the desired suspension is produced. The suspension thus obtained may be homogenized and deaerated prior to filling of the capsules.

The antacid capsules according to the invention will contain an amount of calcium carbonate suspension effective to neutralize the desired amount of hydrochloric acid per capsule. Preferably, the high concentration of the antacid suspension according to the invention is used to advantage in providing capsules with a larger acid neutralizing capacity than heretofore feasible, such as about 15 mEq/capsule. However, the advantages of the present invention are also achieved by providing capsules with any desired acid neutralizing capacity, such as about 10 mEq./capsule, since such capsules will be substantially smaller than prior art capsules of the same capacity. Usefully, the amount of antacid suspension per capsule will be chosen to provide from about 5 to about 15 mEq, such as from about 10 to about 15 mEq, acid neutralizing capacity per capsule.

The present invention is illustrated in terms of its preferred embodiment in the following examples. In this specification and the appended claims, all parts and percentages are by weight, unless otherwise stated.

EXAMPLE 1

An antacid suspension was prepared from the following materials:

|  | Parts |
| --- | --- |
| Ground Limestone | 1000 |
| Polyethylene Glycol 400, NF | 500 |
| Cross-linked carboxymethylcellulose sodium, NF | 8 |

A high speed propeller mixer provided with a scraper was charged with the PEG-400, and the cross-linked CMC sodium was added, while stirring. After all lumps were broken up and a uniform slurry was obtained, the ground limestone was added in portions, and stirring was continued until all of the solids were suspended. The resulting slurry was homogenized and dearated and then filled into #11 oblong A size soft gelatin capsules by means of a rotary die encapsulator. The shell of the capsules was formed from gelatin, water, sorbitol and glycerin, and contained vanillin flavoring agent and titanium dioxide opacifier.

The resulting capsules were 0.6 ml in size and each contained:

| $CaCO_3$ | 750 mg. |
| --- | --- |
| PEG-400 | 374 mg. |
| CMC-Na | 6 mg. |
| Total | 1130 mg. |

The ground limestone particles used in this Example are shown in the FIGURE and had a particle size distribution as follows:

|  | Percent |
| --- | --- |
| Smaller than 1 micron | 15 |
| 1 to 10 microns | 80 |
| Larger than 10 microns | 5 |

The antacid suspension was pourable and was pumpable by a positive displacement pump.

EXAMPLE 2

The capsules prepared in Example 1 were analyzed for acid neutralizing capacity by charging a 250 ml beaker with 70 ml of water that is then warmed to 37° C. One capsule is added and the water is stirred until the capsule ruptures. Thereafter the procedure in the FDA acid neutralizing capacity test in 21 CFR §331.26(c) is followed. The capsules of Example 1 were found to contain at least 15 mEq. acid neutralizing capacity.

I claim:

1. A pourable and pumpable antacid suspension, which comprises from about 60 to about 70%, by weight, based on the weight of the suspension, of calcium carbonate particles suspended in a pharmaceutically acceptable non-aqueous liquid carrier compatible with an acid- and water-soluble capsule shell material and containing less than about 5% by weight of water, based on the weight of the liquid carrier, said calcium carbonate particles containing more than about 50%, by weight, of particles in the range of from about 1 to about 10 microns, based on the weight of said particles, said calcium carbonate particles being irregularly shaped and having a plurality of edges formed by the intersection of substantially planar surfaces.

2. The antacid suspension according to claim 1, wherein at least 65% by weight of said particles is in said range of from about 1 to about 10 microns.

3. The antacid suspension according to claim 2, wherein the amount of said particles above about 10 microns is from 0 to about 10% by weight.

4. The antacid suspension according to claim 1, wherein from about 75 to about 100% of said particles is in said range of from about 1 to about 10 microns, from about 0 to about 15% is below about 1 micron and from about 0 to about 10% are above about 10 microns, all by weight based on the weight of said particles.

5. The antacid suspension according to claim 1, wherein said liquid carrier is a polyethylene glycol or mixture thereof having an average molecular weight of from about 200 to about 600.

6. The antacid suspension according to claim 5, wherein said liquid carrier is PEG-400.

7. The antacid suspension according to claim 1, which comprises a suspending agent.

8. An antacid in unit dosage form, which comprises an effective amount of the antacid suspension of claim 1 capsulated within a capsule shell.

9. The antacid according to claim 8, wherein said capsule shell is gelatin.

* * * * *